United States Patent
Maekawa et al.

(10) Patent No.: US 9,539,642 B2
(45) Date of Patent: *Jan. 10, 2017

(54) METHOD FOR INCREASING PRODUCTION VOLUME OF FINE PARTICLES USING FORCED THIN FILM FLUID TREATMENT APPARATUS

(75) Inventors: Masaki Maekawa, Izumi (JP); Kaeko Araki, Izumi (JP); Daisuke Honda, Izumi (JP); Masakazu Enomura, Izumi (JP)

(73) Assignee: M. TECHNIQUE CO., LTD., Izumi-Shi (JP)

( * ) Notice: Subject to any disclaimer, the term of this patent is extended or adjusted under 35 U.S.C. 154(b) by 301 days.

This patent is subject to a terminal disclaimer.

(21) Appl. No.: 14/123,051

(22) PCT Filed: Mar. 15, 2012

(86) PCT No.: PCT/JP2012/056734
§ 371 (c)(1),
(2), (4) Date: Nov. 27, 2013

(87) PCT Pub. No.: WO2012/164999
PCT Pub. Date: Dec. 6, 2012

(65) Prior Publication Data
US 2014/0121336 A1    May 1, 2014

(30) Foreign Application Priority Data

May 28, 2011 (JP) ................................. 2011-119800
May 30, 2011 (JP) ................................. 2011-121037

(51) Int. Cl.
*B01J 13/00* (2006.01)
*B22F 9/16* (2006.01)
(Continued)

(52) U.S. Cl.
CPC ............... *B22F 9/16* (2013.01); *B01F 3/1221* (2013.01); *B01F 7/00775* (2013.01);
(Continued)

(58) Field of Classification Search
CPC . B01F 3/1221; B01F 7/00775; B01F 7/00791; B22F 9/16; B01J 19/1887; C07D 471/04; C01G 23/08
See application file for complete search history.

(56) References Cited

U.S. PATENT DOCUMENTS

2004/0032792 A1    2/2004  Enomura
2004/0090862 A1*   5/2004  Uesugi ................. B01F 3/0807
                                                                    366/331
(Continued)

FOREIGN PATENT DOCUMENTS

CN    101612533 A    12/2009
CN    101795772 A    8/2010
(Continued)

OTHER PUBLICATIONS

Machine Translation of Publ. No. JP 2006-341232, published Dec. 2006, Japan Patent Office, Tokyo, Japan, online at https://dossier1.j-platpat.inpit.go.jp/tri/all/odse/ODSE_GM101_Top.action (Downloaded Sep. 30, 2015), pp. 1-26.*

*Primary Examiner* — Daniel S Metzmaier
(74) *Attorney, Agent, or Firm* — Birch, Stewart, Kolasch & Birch, LLP (57) ABSTRACT

A method for increasing the production of fine particles is provided. The method uses at least two types of fluids to be processed, a raw material fluid containing at least one type of fine particle raw material and a fluid for treating the fine particle raw material. Fine particles are obtained by mixing the fluids to be processed in a thin film fluid formed between at least two processing surfaces which are disposed to be faced with each other so as to be able to approach to and (Continued)

separate from each other, at least one of which rotates relative to the other. The production of the fine particles is increased by introducing the raw material fluid from the centers of the processing surfaces.

8 Claims, 5 Drawing Sheets

(51) Int. Cl.
  *B01F 7/00* (2006.01)
  *B01J 19/18* (2006.01)
  *C01G 23/08* (2006.01)
  *C07D 471/04* (2006.01)
  *B01F 3/12* (2006.01)

(52) U.S. Cl.
  CPC ....... *B01F 7/00791* (2013.01); *B01J 19/1887* (2013.01); *C01G 23/08* (2013.01); *C07D 471/04* (2013.01)

(56) References Cited

U.S. PATENT DOCUMENTS

| | | |
|---|---|---|
| 2010/0155310 A1 | 6/2010 | Enomura |
| 2010/0326321 A1 | 12/2010 | Enomura |
| 2014/0110336 A1* | 4/2014 | Araki ................ B01D 11/0461 210/634 |
| 2014/0110884 A1* | 4/2014 | Araki ................ B01F 7/00775 264/300 |
| 2014/0155247 A1* | 6/2014 | Aoyagi ............... B01D 9/0054 501/134 |

FOREIGN PATENT DOCUMENTS

| | | |
|---|---|---|
| EP | 2 180 021 A1 | 4/2010 |
| EP | 2184109 A1 | 5/2010 |
| EP | 2 204 351 A1 | 7/2010 |
| JP | 2004-049957 A | 2/2004 |
| JP | 2004-211156 A | 7/2004 |
| JP | 2006-341232 A | 12/2006 |
| JP | 2009-082902 A | 1/2009 |
| WO | WO 2009-008388 A1 | 1/2009 |
| WO | WO 2009-008393 A1 | 1/2009 |

* cited by examiner

METHOD FOR INCREASING PRODUCTION VOLUME OF FINE PARTICLES USING FORCED THIN FILM FLUID TREATMENT APPARATUS

The present invention relates to a method for increasing production of fine particles using forced thin film fluid treatment apparatus.

Fine particles are wanted in the entire industrial fields, wherein it is necessary to selectively produce fine particles whose size is from a micrometer to a nanometer in accordance with the intended use thereof. Especially, nanoparticles (fine particles with the size of nanometers), the fine particles whose diameter is less than 1 μm, express new characteristics that are different from those of particles; and therefore, a new industrial method for producing nanoparticles is wanted to be developed. In fine particles with the size of micrometers too, there have been problems of reproducibility and energy cost in conventional methods; and thus, demand on the method for producing fine particles with which particle diameter thereof can be easily controlled from micrometers to nanometers is growing. Simultaneously with this, demand on the throughput in production of fine particles is growing; and thus, similarly to control of the particle diameter, a method for producing fine particles with a high throughput is wanted.

In order to solve subjects and problems of the conventional technology, called as "a microchemical process technology", the present applicant provided a method for producing nanoparticles (Patent Document 2) by using stirring and instantaneous/uniform mixing of a plurality of fluids in a narrow flow path based on the microchemical process with a totally new concept, more precisely, based on the principle of the apparatus shown in Patent Document 1 filed by the present applicant. This apparatus makes use of the principle of a mechanical seal, wherein a forced thin film fluid of a fluid to be processed is formed between processing surfaces which relatively moves so as to be able to approach to and separate from each other, and the said fluid to be processed is charged into between the rotating processing surfaces, whereby realizing to make the distance between the processing surfaces a minute space by a pressure balance between the supply pressure of the fluid and the pressure applied between the rotating processing surfaces. In the methods before the method based on the above-mentioned principle, the distance between these processing surfaces was controlled by a mechanical means and the like; but in these methods, a heat generated by rotation, a deformation or a misalignment of an axis caused by it, and others could not be absorbed; and thus, to realize the minute distance between the processing surfaces, at least 10 μm or less for this distance, had been substantially impossible. That is, by using the principle of the apparatus in Patent Document 1, production of nanoparticles became possible by instantaneous chemical reaction, physicochemical reaction, or the like in the minute flow path; and inventors of the present application further carried out an extensive investigation, and as result, surprisingly, instantaneous stirring, mixing, reaction; and separation could be realized in a minute flow path of 0.1 to 10 μm, without saying 1 mm or less.

Methods proposed in Patent Documents 2 and 3 for producing fine particles are extremely effective methods for producing fine particles because these methods can produce fine particles with a low cost and a low energy; in these Patent Documents, there is a specific disclosure with regard to, for example, the case that, in order to increase the throughput, concentration and introduction rate of a raw material of fine particles that is contained in a second fluid (fluid that is introduced from the introduction flow path having an opening in the processing surface) are made higher whereby changing particle diameter of the fine particles. However, the disclosure therein alone is not necessarily satisfactory to secure the required throughput; and thus, a method for increasing the throughput further has been eagerly wanted in this production method.

PRIOR ART DOCUMENTS

Patent Document

Patent Document 1: Japanese Patent Laid-Open publication No. 2004-49957
Patent Document 2: International Patent Laid-Open Publication No. 2009/008393
Patent Document 3: International Patent Laid-Open Publication No. 2009/008388

DISCLOSURE OF THE INVENTION

Problems to be Solved by the Invention

In view of the above-mentioned, the present invention has an object to provide a novel method for increasing a throughput in production of fine particles.

Means for Solving the Problems

The present invention provides a method for increasing production volume of fine particles, wherein using at least two fluids as fluids to be processed,
of these fluids, at least one fluid is a raw material fluid which contains at least one kind of the fine particle raw material, at least one fluid other than the said fluid is a fluid to process the fine particle raw material, wherein
the said two or more fluids to be processed are mixed in a thin film fluid formed between at least two processing surfaces which are disposed in a position they are faced with each other so as to be able to approach to and separate from each other, at least one of which rotates relative to the other, thereby obtaining the fine particles in the method for producing fine particles, wherein
the raw material fluid is introduced from a center of the at least two processing surfaces which are disposed in a position they are faced with each other so as to be able to approach to and separate from each other, at least one of which rotates relative to the other.

The present invention may be carried out as at least one process selected from separation, emulsification, dispersion, reaction, and aggregation.

The present invention may be carried out as a process, wherein the raw material fluid passes through between both the processing surfaces while forming the thin film fluid, another introduction path independent of the flow path which the raw material fluid is passed is provided, and at least one opening leading to a different introduction path is arranged; the at least one other kind of a fluid is introduced between the processing surfaces through the opening, whereby mixing the raw material fluid with the at least one other kind of the fluid in the thin film fluid.

In addition, the present invention may be carried out as a process, wherein at least one of the processing surfaces is in the form of a ring, through a center of which the raw material fluid is introduced into between the processing surfaces, wherein a total open area (a) of a space between both the processing surfaces in the nearest point to a center of the ring, in which space the raw material fluid and the at least one other kind of the fluid are joined together, is 5 or less times relative to a total open area (b) of the opening leading to the another introduction path.

In addition, the present invention may be carried out as a process, wherein at least one of the processing surfaces is in the form of a ring, through a center of which the raw material fluid is introduced into between the processing surfaces; at least two or more openings of the another introduction path leading to between the processing surfaces are provided, and a total open area (a) of a space between both the processing surfaces in the nearest point to the center of the ring, in which space the raw material fluid and the at least one other kind of the fluid are joined together, is 5 or less times relative to each open area of the openings that lead to the another introduction path.

In addition, the present invention may be carried out as a process, wherein a form of the opening of another introduction flow path leading to the processing surface is a circular ring.

Further in addition, the present invention may be carried out as a process, wherein at least one of the processing surfaces is in the form of a ring, from a center of which the raw material fluid is introduced into between the processing surfaces, and a flow amount per unit time of the raw material fluid introduced into between the processing surfaces from the center of this ring is in the range of 0.1 to 20000 times relative to a flow amount per unit time of the at least one other fluid that is introduced from the opening.

The present invention is carried out suitably by using an apparatus provided with: a fluid pressure imparting mechanism for imparting a pressure to the fluids to be processed, a first processing member is provided with a first processing surface of the two processing surfaces, a second processing member is provided with a second processing surface of the two processing surfaces, and a rotation drive mechanism for rotating these processing members relative to each other; of the first processing member and the second processing member, at least the second processing member is provided with a pressure-receiving surface, and at least part of the pressure-receiving surface is comprised of the second processing surface, wherein and this pressure-receiving surface receives a pressure applied to the fluids to be processed by the fluid pressure imparting mechanism thereby generating a force to move in the direction of separating the second processing surface from the first processing surface.

Advantages

In the method for producing fine particles by introducing a fluid to be processed into between at least two processing surfaces which are disposed in a position they are faced with each other so as to be able to approach to and separate from each other, at least one of which rotates relative to the other, thereby obtaining fine particles in a thin film formed between the processing surfaces, it was found by the present invention that, in the processing surfaces, a flow amount or a flow rate, i.e., a flow amount per unit time, of the fluid to be processed that can be charged into between the processing surfaces from the first introduction part d1 which is located in a center of the circular processing surface (the utmost upstream side) can be made larger than a flow amount or a flow rate charged from the second introduction part d2 leading to an opening arranged in the processing surface, and further found that, of the fluids to be processed that are introduced between the processing surfaces, if a raw material fluid is introduced into between the processing surfaces from the center of the processing surface, a production volume of fine particles can be increased; and based on these findings, the present invention could be completed, whereby providing a novel method for increasing a production volume of fine particles.

MODES FOR CARRYING OUT THE INVENTION

Hereinafter, the present invention will be explained in detail by referring to an example of the embodiments of the present invention. However, technical scope of the present invention is not restricted by the following embodiments and Examples.

Figure 1:
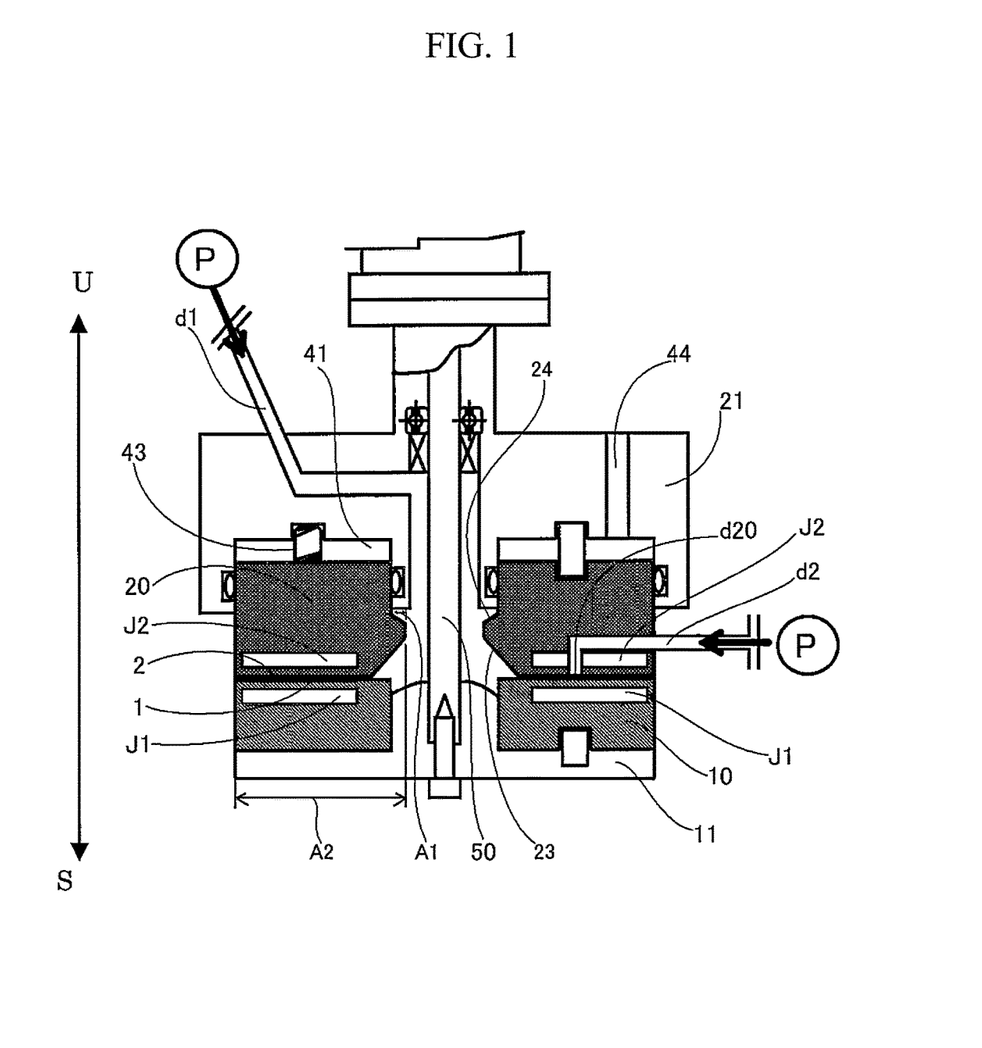
FIG. 1 is a schematic sectional view showing the fluid processing apparatus according to an embodiment of the present application of the invention.
Figure 2:
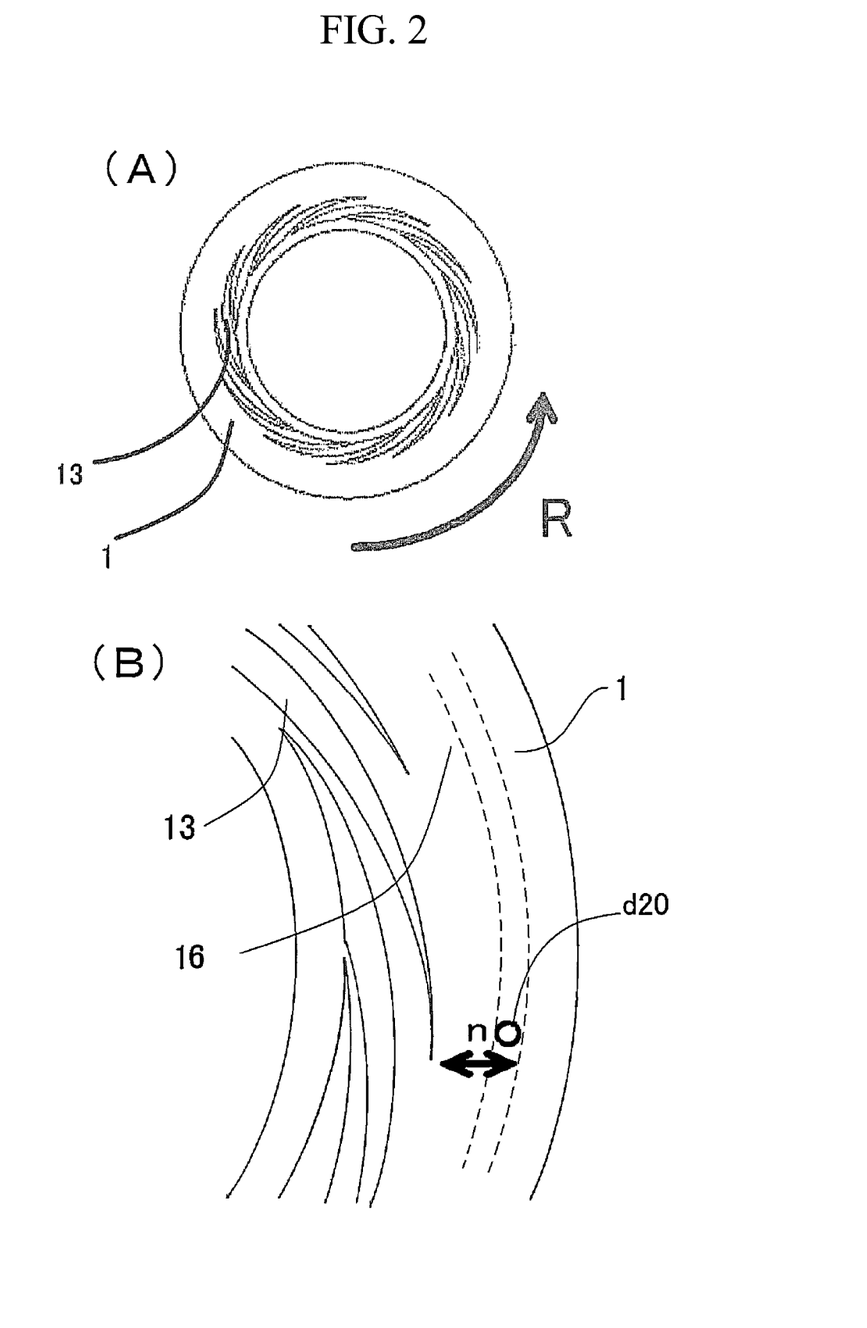
FIG. 2(A) is a schematic plane view of the first processing surface in the fluid processing apparatus shown in FIG. 1.
FIG. 2(B) is an enlarged view showing an important part of the processing surface in the apparatus.
Figure 3:
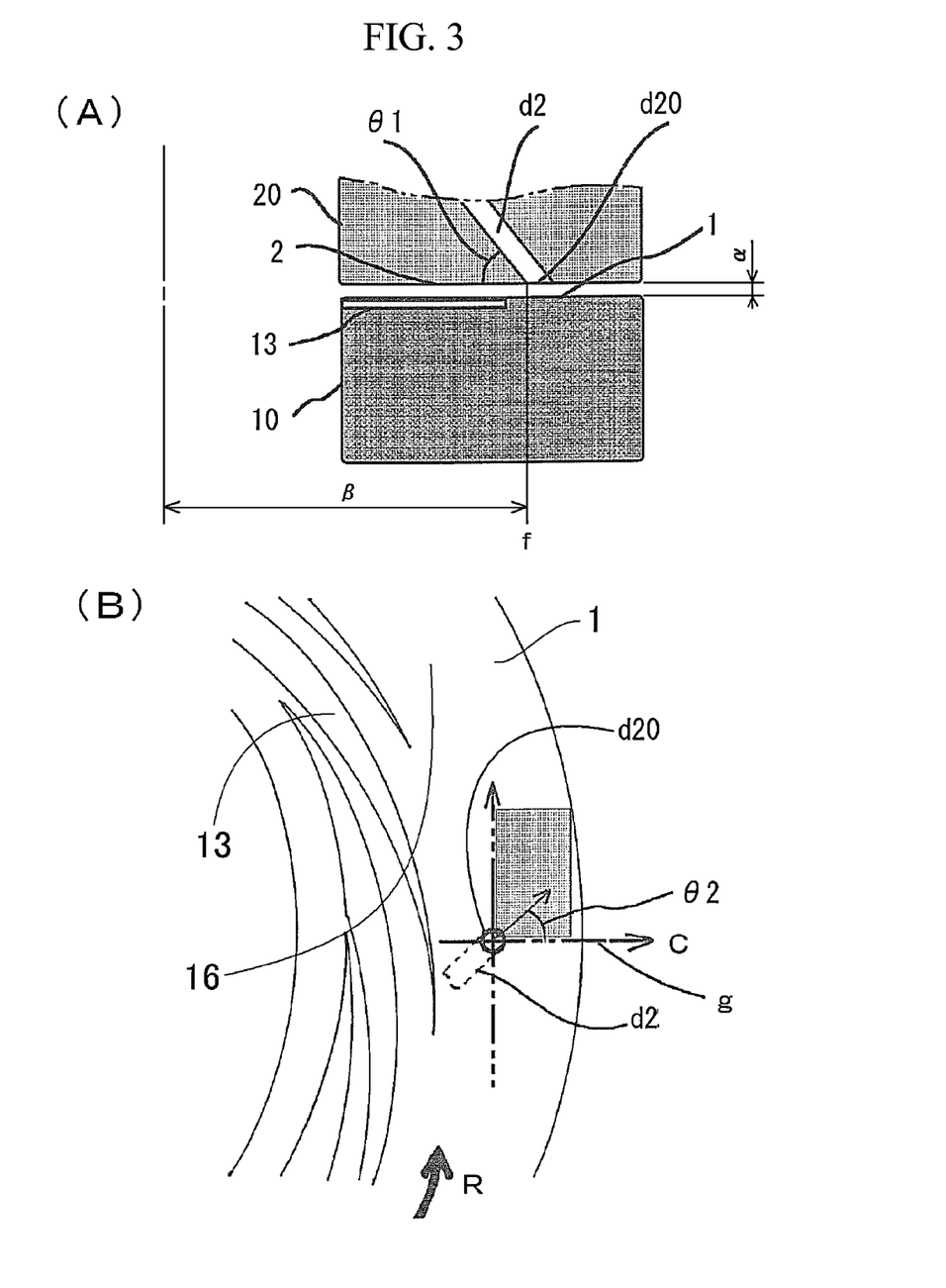
FIG. 3(A) is a sectional view of the second introduction member of the apparatus.
FIG. 3(B) is an enlarged view showing an important part of the processing surface for explaining the second introduction member.

The fluid processing apparatus shown in FIG. 1 to FIG. 3 is similar to the apparatus described in Patent Document 2 and 3, with which a material to be processed is processed between processing surfaces in processing members arranged so as to be able to approach to and separate from each other, at least one of which rotates relative to the other; wherein, of the fluids to be processed, a first fluid to be processed, i.e., a first fluid, is introduced into between the processing surfaces, and a second fluid to be processed, i.e., a second fluid, is introduced into between the processing surfaces from a separate path that is independent of the flow path introducing the first fluid and has an opening leading to between the processing surfaces, whereby the first fluid and the second fluid are mixed and stirred between the processing surfaces. Meanwhile, in FIG. 1, a reference character U indicates an upside and a reference character S indicates a downside; however, up and down, front and back and right and left shown therein indicate merely a relative positional relationship and does not indicate an absolute position. In FIG. 2(A) and FIG. 3(B), reference character R indicates a rotational direction. In FIG. 3(B), reference character C indicates a direction of centrifugal force (a radial direction).

In this apparatus provided with processing surfaces arranged opposite to each other so as to be able to approach to and separate from each other, at least one of which rotates relative to the other, at least two kinds of fluids as fluids to be processed are used, wherein at least one fluid thereof contains at least one kind of material to be processed, a thin film fluid is formed by converging the respective fluids between these processing surfaces, and the material to be processed is processed in this thin film fluid. With this apparatus, mentioned-above, a plurality of fluids to be processed may be processed; but a single fluid to be processed may be processed as well.

This fluid processing apparatus is provided with two processing members of a first processing member 10 and a second processing member 20 arranged opposite to each other, wherein at least one of these processing members rotates. The surfaces arranged opposite to each other of the respective processing members 10 and 20 are made to be the respective processing surfaces. The first processing member 10 is provided with a first processing surface 1 and the second processing member 20 is provided with a second processing surface 2.

The processing surfaces 1 and 2 are connected to a flow path of the fluid to be processed and constitute part of the flow path of the fluid to be processed. Distance between these processing surfaces 1 and 2 can be changed as appropriate; and thus, the distance thereof is controlled so as to form a minute space usually in the range of 1 μm to 1 mm, especially 1 μm to 10 μm. With this, the fluid to be processed passing through between the processing surfaces 1 and 2 becomes a forced thin film fluid forced by the processing surfaces 1 and 2.

With this apparatus, when a plurality of fluids to be processed are processed, the apparatus is connected to a flow path of the first fluid to be processed whereby forming part of the flow path of the first fluid to be processed; and part of the flow path of the second fluid to be processed other than the first fluid to be processed is formed. In this apparatus, the two paths converge into one, and two fluids to be processed are mixed between the processing surfaces 1 and 2 so that the fluids may be processed by reaction and so on. It is noted here that the term "process(ing)" includes not only the embodiment wherein a material to be processed is reacted but also the embodiment wherein a material to be processed is only mixed or dispersed without accompanying reaction.

To specifically explain, this apparatus is provided with a first holder 11 for holding the first processing member 10, a second holder 21 for holding the second processing member 20, a surface-approaching pressure imparting mechanism, a rotation drive mechanism, a first introduction part d1, a second introduction part d2, and a fluid pressure imparting mechanism p.

As shown in FIG. 2(A), in this embodiment, the first processing member 10 is a circular body, specifically a disk with a ring form. Similarly, the second processing member 20 is a circular disk. Material of the processing members 10 and 20 is not only metal and carbon, but also ceramics, sintered metal, abrasion-resistant steel, sapphire, and other metal subjected to hardening treatment, and rigid material subjected to lining, coating, or plating. In the processing members 10 and 20 of this embodiment, at least part of the first and the second surfaces 1 and 2 arranged opposite to each other is mirror-polished.

Roughness of this mirror polished surface is not particularly limited; but surface roughness Ra is preferably 0.01 μm to 1.0 μm, or more preferably 0.03 μm to 0.3 μm.

At least one of the holders can rotate relative to the other holder by a rotation drive mechanism such as an electric motor (not shown in drawings). A reference numeral 50 in FIG. 1 indicates a rotary shaft of the rotation drive mechanism; in this embodiment, the first holder 11 attached to this rotary shaft 50 rotates, and thereby the first processing member 10 attached to this first holder 11 rotates relative to the second processing member 20. As a matter of course, the second processing member 20 may be made to rotate, or the both may be made to rotate. Further in this embodiment, the first and second holders 11 and 21 may be fixed, while the first and second processing members 10 and 20 may be made to rotate relative to the first and second holders 11 and 21.

At least any one of the first processing member 10 and the second processing member 20 is able to approach to and separate from at least any other member, thereby the processing surfaces 1 and 2 are able to approach to and separate from each other.

In this embodiment, the second processing member 20 approaches to and separates from the first processing member 10, wherein the second processing member 20 is accepted in an accepting part 41 arranged in the second holder 21 so as to be able to rise and set. However, as opposed to the above, the first processing member 10 may approach to and separate from the second processing member 20, or both the processing members 10 and 20 may approach to and separate from each other.

This accepting part 41 is a concave portion for mainly accepting that side of the second processing member 20 opposite to the second processing surface 2, and this concave portion is a groove being formed into a circle, i.e., a ring when viewed in a plane. This accepting part 41 accepts the second processing member 20 with sufficient clearance so that the second processing member 20 may rotate. Meanwhile, the second processing member 20 may be arranged so as to be movable only parallel to the axial direction; alternatively, the second processing member 20 may be made movable, by making this clearance larger, relative to the accepting part 41 so as to make the center line of the processing member 20 inclined, namely unparallel, to the axial direction of the accepting part 41, or movable so as to depart the center line of the processing member 20 and the center line of the accepting part 41 toward the radius direction.

It is preferable that the second processing member 20 be accepted by a floating mechanism so as to be movable in the three dimensional direction, as described above.

The fluids to be processed are introduced into between the processing surfaces 1 and 2 from the first introduction part d1 and the second introduction part d2, the flow paths through which the fluids flow, under the state that pressure is applied thereto by a fluid pressure imparting mechanism p consisting of various pumps, potential energy, and so on. In this embodiment, the first introduction part d1 is a path arranged in the center of the circular, second holder 21, and one end thereof is introduced into between the processing surfaces 1 and 2 from inside the circular, processing members 10 and 20. Through the second introduction part d2, the first fluid to be processed and the second fluid to be processed for reaction are introduced into between the processing surfaces 1 and 2. In this embodiment, the second introduction part d2 is a path arranged inside the second processing member 20, and one end thereof is open at the second processing surface 2. The first fluid to be processed which is pressurized with the fluid pressure imparting mechanism p is introduced from the first introduction part d1 to the space inside the processing members 10 and 20 so as to pass through between the first and processing surfaces 1 and 2 to outside the processing members 10 and 20. From the second introduction part d2, the second fluid to be processed which is pressurized with the fluid pressure imparting mechanism p is provided into between the processing surfaces 1 and 2, whereat this fluid is converged with the first fluid to be processed, and there, various fluid processing such as mixing, stirring, emulsification, dispersion, reaction, deposition, crystallization, and separation are effected, and then the fluid thus processed is discharged from the processing surfaces 1 and 2 to outside the processing members 10 and 20. Meanwhile, an environment outside the processing members 10 and 20 may be made negative pressure by a vacuum pump.

The surface-approaching pressure imparting mechanism mentioned above supplies the processing members with force exerting in the direction of approaching the first processing surface 1 and the second processing surface 2 each other. In this embodiment, the surface-approaching pressure imparting mechanism is arranged in the second holder 21 and biases the second processing member 20 toward the first processing member 10.

The surface-approaching pressure imparting mechanism is a mechanism to generate force (hereinafter, surface-approaching pressure) to press the first processing surface 1 of the first processing member 10 and the second processing surface 2 of the second processing member 20 in the direction to make them approach to each other. The mechanism generates a thin film fluid having minute thickness in a level of nanometer or micrometer by the balance between the surface-approaching pressure and the force to separate the processing surfaces 1 and 2 from each other, i.e., the force such as the fluid pressure. In other words, the distance between the processing surfaces 1 and 2 is kept in a predetermined minute distance by the balance between these forces.

In the embodiment shown in FIG. 1, the surface-approaching pressure imparting mechanism is arranged between the accepting part 41 and the second processing member 20. Specifically, the surface-approaching pressure imparting mechanism is composed of a spring 43 to bias the second processing member 20 toward the first processing member 10 and a biasing-fluid introduction part 44 to introduce a biasing fluid such as air and oil, wherein the surface-approaching pressure is provided by the spring 43 and the fluid pressure of the biasing fluid. The surface-approaching pressure may be provided by any one of this spring 43 and the fluid pressure of this biasing fluid; and other forces such as magnetic force and gravitation may also be used. The second processing member 20 recedes from the first processing member 10 thereby making a minute space between the processing surfaces by separating force, caused by viscosity and the pressure of the fluid to be processed applied by the fluid pressure imparting mechanism p, against the bias of this surface-approaching pressure imparting mechanism. By this balance between the surface-approaching pressure and the separating force as mentioned above, the first processing surface 1 and the second processing surface 2 can be set with the precision of a micrometer level; and thus the minute space between the processing surfaces 1 and 2 may be set. The separating force mentioned above includes fluid pressure and viscosity of the fluid to be processed, centrifugal force by rotation of the processing members, negative pressure when negative pressure is applied to the biasing-fluid introduction part 44, and spring force when the spring 43 works as a pulling spring. This surface-approaching pressure imparting mechanism may be arranged also in the first processing member 10, in place of the second processing member 20, or in both the processing members.

To specifically explain the separation force, the second processing member 20 has the second processing surface 2 and a separation controlling surface 23 which is positioned inside the processing surface 2 (namely at the entering side of the fluid to be processed into between the first and second processing surfaces 1 and 2) and next to the second processing surface 2. In this embodiment, the separation controlling surface 23 is an inclined plane, but may be a horizontal plane. The pressure of the fluid to be processed acts to the separation controlling surface 23 to generate force directing to separate the second processing member 20 from the first processing member 10. Therefore, the second processing surface 2 and the separation controlling surface 23 constitute a pressure receiving surface to generate the separation force.

In the example shown in FIG. 1, an approach controlling surface 24 is formed in the second processing member 20. This approach controlling surface 24 is a plane opposite, in the axial direction, to the separation controlling surface 23 (upper plane in FIG. 1) and, by action of pressure applied to the fluid to be processed, generates force of approaching the second processing member 20 toward the first processing member 10.

Meanwhile, the pressure of the fluid to be processed exerted on the second processing surface 2 and the separation controlling surface 23, i.e., the fluid pressure, is understood as force constituting an opening force in a mechanical seal. The ratio (area ratio A1/A2) of a projected area A1 of the approach controlling surface 24 projected on a virtual plane perpendicular to the direction of approaching and separating the processing surfaces 1 and 2, that is, in the direction of rising and setting of the second processing member 20 (axial direction in FIG. 1), to a total area A2 of the projected area of the second processing surface 2 of the second processing member 20 and the separation controlling surface 23 projected on the virtual plane is called as balance ratio K, which is important for control of the opening force. This opening force can be controlled by the pressure of the fluid to be processed, i.e., the fluid pressure, by changing the balance line, i.e., by changing the area A1 of the approach controlling surface 24.

Sliding surface actual surface pressure P, i.e., the fluid pressure out of the surface-approaching pressures, is calculated according to the following equation:

$$P = P1 \times (K-k) + Ps$$

Here, P1 represents the pressure of a fluid to be processed, i.e., the fluid pressure, K represents the balance ratio, k represents an opening force coefficient, and Ps represents a spring and back pressure.

By controlling this balance line to control the sliding surface actual surface pressure P, the space between the processing surfaces 1 and 2 is formed as a desired minute space, thereby forming a fluid film of the fluid to be processed so as to make the processed substance such as a product fine and to effect uniform processing by reaction.

Meanwhile, the approach controlling surface 24 may have a larger area than the separation controlling surface 23, though this is not shown in the drawing.

The fluid to be processed becomes a forced thin film fluid by the processing surfaces 1 and 2 that keep the minute space therebetween, whereby the fluid is forced to move out from the circular, processing surfaces 1 and 2. However, the first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Meanwhile, a rotary shaft 50 is not only limited to be placed vertically, but may also be placed horizontally, or at a slant. This is because the fluid to be processed is processed in a minute space between the processing surfaces 1 and 2 so that the influence of gravity can be substantially eliminated. In addition, this surface-approaching pressure imparting mechanism can function as a buffer mechanism of micro-vibration and rotation alignment by concurrent use of the foregoing floating mechanism with which the second processing member 20 may be held displaceably.

In the first and second processing members 10 and 20, the temperature thereof may be controlled by cooling or heating at least any one of them; in FIG. 1, an embodiment having temperature regulating mechanisms J1 and J2 in the first and second processing members 10 and 20 is shown. Alternatively, the temperature may be regulated by cooling or heating the introducing fluid to be processed. These temperatures may be used to separate the processed substance or may be set so as to generate Benard convection or Marangoni convection in the fluid to be processed between the first and second processing surfaces 1 and 2.

As shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1 as shown in FIG. 2(B), or, though not shown in the drawing, may be extended straight radially, or bent at a right angle, or jogged; and the concave portion may be continuous, intermittent, or branched. In addition, this depression 13 may be formed also on the second processing surface 2, or on both the first and second processing surfaces 1 and 2. By forming the depression 13 as mentioned above, the micro-pump effect can be obtained so that the fluid to be processed may be sucked into between the first and second processing surfaces 1 and 2.

It is preferable that the base edge of this depression 13 reach the inner periphery of the first processing member 10. The front edge of the depression 13 is extended to the direction of the outer periphery of the first processing surface 1; the depth thereof (cross section area) is made gradually shallower (smaller) from the base edge to the front edge.

Between the front edge of the depression 13 and the outer peripheral of the first processing surface 1 is formed the flat plane 16 not having the depression 13.

When an opening d20 of the second introduction part d2 is arranged in the second processing surface 2, the arrangement is done preferably at a position opposite to the flat surface 16 of the first processing surface 1 arranged at a position opposite thereto.

This opening d20 is arranged preferably in the downstream (outside in this case) of the depression 13 of the first processing surface 1. The opening is arranged especially preferably at a position opposite to the flat surface 16 located nearer to the outer diameter than a position where the direction of flow upon introduction by the micro-pump effect is changed to the direction of a spiral and laminar flow formed between the processing surfaces. Specifically, in FIG. 2(B), a distance n from the outermost side of the depression 13 arranged in the first processing surface 1 in the radial direction is preferably about 0.5 mm or more. Especially in the case of separating fine particles from a fluid, it is preferable that mixing of a plurality of fluids to be processed and separation of the fine particles therefrom be effected under the condition of a laminar flow. The form of the opening d20 may be a circular form as shown by the solid lines in FIG. 2(B) and FIG. 3(B), or a concentric circular ring form that surrounds the central opening of the processing surface 2 as shown by the dotted lines in FIG. 2(B). If the circular ring opening d20 is arranged concentrically to the central opening of the processing surface 2, the same condition in the circumferential direction may be applied upon introduction of the second fluid into between the processing surfaces 1 and 2. Alternatively, the circular ring opening d20 may not be arranged concentrically to the central opening of the processing surface 2. In addition, the circular ring opening d20 may be continuous or discontinuous.

This second introduction part d2 may have directionality. For example, as shown in FIG. 3(A), the direction of introduction from the opening d20 of the second processing surface 2 is inclined at a predetermined elevation angle ($\theta 1$) relative to the second processing surface 2. The elevation angle ($\theta 1$) is set at more than 0° and less than 90°, and when the reaction speed is high, the angle ($\theta 1$) is preferably set in the range of 1° to 45°.

In addition, as shown in FIG. 3(B), introduction from the opening d20 of the second processing surface 2 has directionality in a plane along the second processing surface 2. The direction of introduction of this second fluid is in the outward direction departing from the center in a radial component of the processing surface and in the forward direction in a rotation component of the fluid between the rotating processing surfaces. In other words, a predetermined angle ($\theta 2$) exists facing the rotation direction R from a reference line g, which is the line to the outward direction and in the radial direction passing through the opening d20. This angle ($\theta 2$) is also set preferably at more than 0° and less than 90°.

This angle ($\theta 2$) can vary depending on various conditions such as the type of fluid, the reaction speed, viscosity, and the rotation speed of the processing surface. In addition, it is also possible not to give the directionality to the second introduction part d2 at all.

In the embodiment shown in FIG. 1, kinds of the fluid to be processed and numbers of the flow path thereof are set two respectively; but they may be one, or three or more. In the embodiment shown in FIG. 1, the second fluid is introduced into between the processing surfaces 1 and 2 from the introduction part d2; but this introduction part may be arranged in the first processing member 10 or in both. Alternatively, a plurality of introduction parts may be arranged relative to one fluid to be processed. The opening for introduction arranged in each processing member is not particularly restricted in its form, size, and number; and these may be changed as appropriate. The opening for introduction may be arranged just before the first and second processing surfaces 1 and 2 or in the side of further upstream thereof.

Meanwhile, because it is good enough only if the reaction could be effected between the processing surfaces 1 and 2, as opposed to the foregoing method, a method wherein the second fluid is introduced from the first introduction part d1 and a solution containing the first fluid is introduced from the second introduction part d2 may also be used. That is, the expression "first" or "second" for each fluid has a meaning for merely discriminating an $n^{th}$ fluid among a plurality of the fluids present; and therefore, a third or more fluids can also exist.

As discussed above, the processing apparatus may be provided with the third introduction part d3, in addition to the first introduction part d1 and the second introduction part d2; and in this case, from each introduction part, for example, the first fluid, the second fluid, and the third fluid respectively may be introduced into the processing apparatus separately. By so doing, concentration and pressure of each fluid can be controlled separately so that the process to obtain the fine particles and the fine particles to be obtained, stabilization of the particle diameter of the fine particles, and so on can be controlled more precisely. Meanwhile, a combination of the fluids to be processed (first to third fluids) that are introduced into the respective introduction parts may be set arbitrarily. The same is applied if the forth or more introduction parts are arranged; and by so doing, fluids to be introduced into the processing apparatus may be subdivided.

In addition, temperatures of the fluids to be processed such as the first fluid, the second fluid, and so on may be controlled; and temperature difference among the first fluid, the second fluid, and so on (namely, temperature difference among each of the supplied fluids to be processed) may be controlled either. To control temperature and temperature difference of each of the supplied fluids to be processed, a mechanism with which temperature of each of the fluids to be processed is measured (temperature of the fluid before introduction to the processing apparatus, or in more detail, just before introduction into between the processing surfaces 1 and 2) so that each of the fluids to be processed that is introduced into between the processing surfaces 1 and 2 may be heated or cooled may be installed.

Regardless of the number of the flow paths, the present invention may be carried out by introducing the raw material fluid, which is a fluid containing at least one fine particle raw material (this will be explained later) from the first introduction part d1. In the processing surface, a flow amount or a flow rate, i.e., a flow amount per unit time, of the fluid that can be charged from the first introduction part d1 which is located in the center of the processing surface (the utmost upstream side) can be made larger than a flow amount or the flow rate charged from the second introduction part d2 leading to the opening arranged in the processing surface, so that a flow amount or a flow rate of the raw material fluid passing thorough between the processing surfaces may be made substantially large. As a result, per unit time in a production volume of fine particles obtained between the processing surfaces may be increased, so that the production volume may be increased as compared with the technical content so far disclosed.

In this embodiment, both the first and the second processing surfaces 1 and 2 are in the form of a ring having opening in the center thereof; however, an embodiment may also be possible that any one of the processing surfaces 1 and 2 is in the form of a ring having opening in the center thereof while the other is not arranged with the opening in the center thereof. The total open area (a) of the space between the first and the second processing surfaces 1 and 2 in this central first introduction part d1 is preferably 5 or less times relative to the total open area (b) of the opening d20. Note here that, the total open area (a) means the total open area between both the processing surfaces in the nearest point "f" to the center of the ring (hereinafter, this point is referred to as the nearest point "f") at which point the first fluid and the second fluid are joined together (see, FIG. 3(A)). Specifically, the total open area (a) is obtained by multiplying the circumference of the circle having the radius β, which is the distance from the center of the first and the second processing surfaces 1 and 2 to the nearest point "f", by α which is the distance between the first and the second processing surfaces 1 and 2.

The nearest point "f" means the innermost side in the opening d20 (the point near to the center in the radius direction); and when two or more openings 20 are arranged, this means the innermost radius side thereof.

Figure 4:
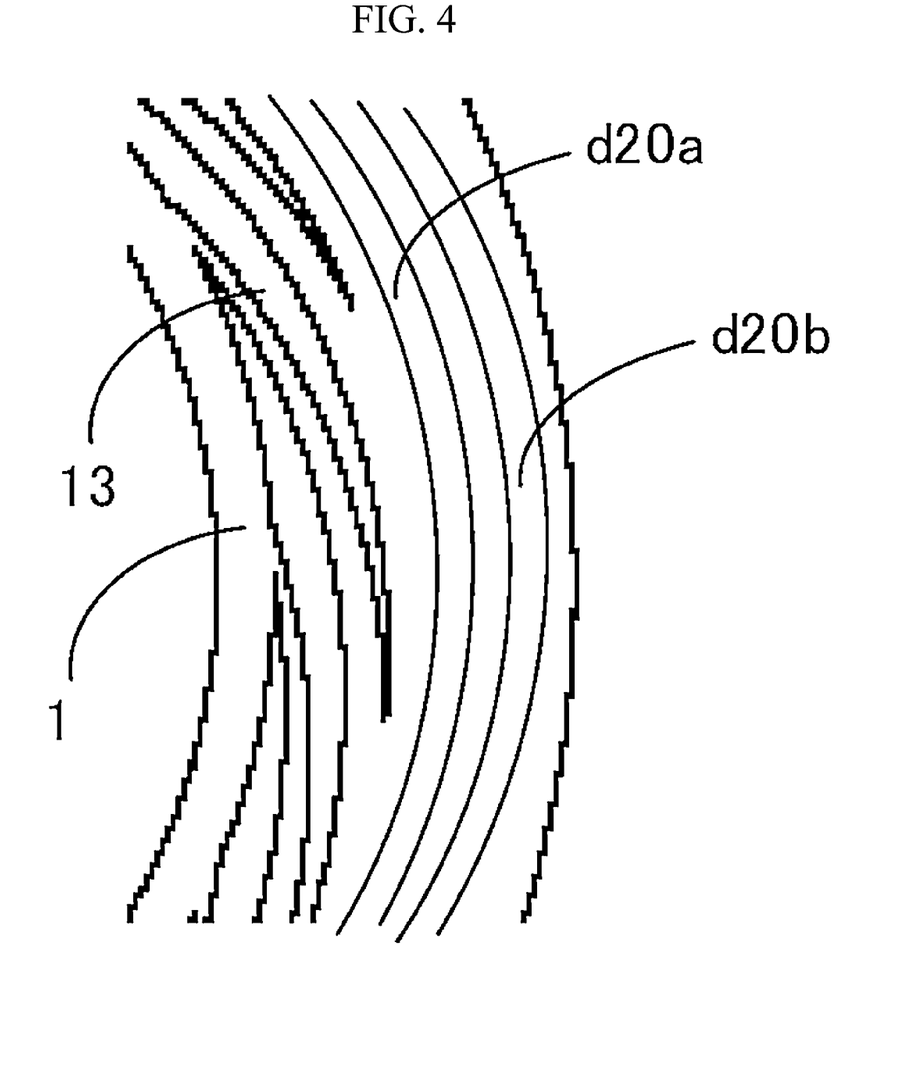
FIG. 4 is an enlarged view showing an important part of the modified processing surface in the apparatus.

Meanwhile, when two or more of the openings d20a and d20b are arranged as shown in FIG. 4, the total open area (a) at the nearest point "f" is preferably 5 or less times relative to the each open area of the opening d20a a and the opening d20b.

The total open area (a) at the nearest point "f" is preferably 5 or less times, but more preferably 3 or less times, or still more preferably 2 or less times, relative to the total open area (b) of the opening d20. Further, the lower limit thereof is not particularly restricted, but preferably 0.001 or more times, or more preferably 0.01 or more times in reality.

Furthermore, the flow amount per unit time of the raw material fluid from the center of the first introduction part d1 is preferably in the range of 0.1 to 20000 times relative to the flow amount per unit time of the at least one other fluid from the second introduction part d2. If it is less than 0.1 times, the flow amount introduced from the center cannot be increased so much, thereby decreasing the effect. Even if the flow amount exceeds 20000 or more times, there is no particular problem; but there is a risk of causing problems such as extremely small total flow amount of the second introduction part d2 and imbalance of the entire system.

In the above-mentioned apparatus, a reaction such as separation/precipitation/emulsification and crystallization is effected while the fluids are being mixed forcibly and uniformly between the processing surfaces 1 and 2 which are disposed in a position they are faced with each other so as to be able to approach to and separate from each other, at least one of which rotates relative to the other, as shown in FIG. 1. Particle diameter and monodispersity of the fine particles to be obtained can be controlled by appropriately controlling rotation speed of the processing members 10 and 20, distance between the processing surfaces 1 and 2, concentration of raw materials, kind of solvents, and so forth.

In the present invention, the at least one kind of fine particle raw material contained in the raw material fluid is not particularly restricted. All substances that are intended to be obtained as fine particles may be used as the fine particle raw material to be obtained as the target. Illustrative example thereof includes an inorganic substance, an organic substance, and an inorganic-organic complex substance, including a metal, a nonmetal, an organic and/or inorganic compound of a metal and a nonmetal, a pigment, a biologically ingestible substance (a compound used as a medical drug and a substance to be ingested into a living body), a resin, and an oil ingredient, so that all substances that are intended to be processed between the processing surfaces may be mentioned. The fine particle raw material may be introduced between the processing surfaces from the first introduction part d1 as the raw material fluid as it is, or it, may be introduced into between the processing surfaces 1 and 2 as the raw material fluid mixed with and/or dissolved in various solvents such as water and an organic solvent.

In the present invention, the at least one fluid other than the raw material fluid, i.e., the fluid to process the fine particle raw material, is not particularly restricted; and thus, it may be selected arbitrarily in accordance with fine particles to be targeted. The treatment mentioned above is not particularly restricted, and thus, separation, emulsification, dispersion, reaction, aggregation, and the like may be mentioned. For example, in the case that fine particles are obtained by separation and/or emulsification, the present invention may be carried out by mixing a raw material fluid with a fluid to separate and/or emulsify a fine particle raw material contained in the raw material fluid in the thin film fluid formed between at least two processing surfaces which are disposed in a position they are faced with each other so as to be able to approach to and separate from each other, at least one of which rotates relative to the other, thereby obtaining the separated and/or emulsified fine particle raw material as fine particles. Alternatively, in the case that fine particles are obtained by a reducing reaction, the present invention may be carried out by mixing a raw material fluid with a fluid to reduce a fine particle raw material contained in the raw material fluid in the thin film fluid formed between at least two processing surfaces which are disposed in a position they are faced with each other so as to be able to approach to and separate from each other, at least one of which rotates relative to the other, thereby obtaining the reduced fine particle raw material as fine particles. As seen above, before and after the treatment, the raw material of fine particles and the obtained fine particles may be the same substance, or different substances.

In the present invention, a dispersing agent such as a block copolymer, a polymer, and a surfactant may be contained in a fluid which contains a raw material fluid, or in a fluid which contains at least one fluid other than the raw material fluid, or in both of these fluids, to a degree not affecting the present invention. Alternatively, this dispersing agent may be contained in a third fluid other than the fluid which contains the raw material fluid and the fluid which contains at least one kind of fluid other than the raw material fluid.

The method for increasing production volume of fine particles according to the present invention may be used in production of the following fine particles. Note that, the present invention is not applied only to the following examples; it can also be used for producing of fine particles that have been produced by means of conventional methods such as a batch process, a continuous process, a microreactor, and a micromixer.

Thus, the example mentioned above includes:

a reaction to obtain pigment particles by mixing an acidic pigment solution, prepared by dissolving at least one kind of pigment in a strong acid such as sulfuric acid, nitric acid, and hydrochloric acid, with a solution including water (acid pasting method), a reaction to precipitate pigment particles by pouring a pigment solution, prepared by dissolving at least one kind of pigment in an organic solvent, into a poor solvent which is a poor solvent to the said pigment and is compatible with the organic solvent used to prepare the pigment solution (reprecipitation method), or a reaction to obtain pigment particles by mixing a pigment solution, obtained by dissolving at least one kind of pigment either into a pH adjusting acidic or alkaline solution or into a mixed solution of the said pH adjusting solution with an organic solvent, with a pigment-separating solution not showing solubility to the pigment contained in the pigment solution or showing smaller solubility to the pigment than the solvent contained in the pigment solution, and yet being capable of changing pH of the pH adjusting solution.

A reaction to carry metal fine particles on a carbon and a carbon black surface by a liquid phase reduction method (illustrative example of the metal includes at least one metal selected from the group consisting of platinum, palladium, gold, silver, rhodium, iridium, ruthenium, osmium, cobalt, manganese, nickel, iron, chromium, molybdenum, and titanium).

A reaction to produce crystals formed of a fullerene molecule and a fullerene nanowhisker/nanofiber nanotube by mixing a solution containing a first solvent having dissolved therein the fullerene with a second solvent having smaller solubility of the fullerene than the first solvent.

A reaction to reduce a metal compound or a metal ion (illustrative example of the metal includes a precious metal such as gold, silver, ruthenium, rhodium, palladium, osmium, iridium, and platinum, or cupper, or a metal alloy of two or more metals mentioned above).

A reaction to hydrolyze a ceramic raw material (illustrative example of the ceramic raw material includes at least one kind selected from Al, Ba, Mg, Ca, La, Fe, Si, Ti, Zr, Pb, Sn, Zn, Cd, As, Ga, Sr, Bi, Ta, Se, Te, Hf, Ni, Mn, Co, S, Ge, Li, B, and Ce).

A reaction to separate titanium dioxide superfine particles by hydrolysis of a titanium compound (illustrative example of the titanium compound includes at least one kind selected from tetraalkoxy titanium such as tetramethoxy titanium, tetraethoxy titanium, tetra-n-propoxy titanium, tetraisopropoxy titanium, tetra-n-butoxy titanium, tetraisobutoxy titanium, and tetra-t-butoxy titanium, or a derivative of them; and titanium tetrachloride, titanyl sulfate, titanium citrate, and titanium tetranitrate).

A producing reaction to co-precipitate and separate fine particles of a compound semiconductor by joining with an ion-containing fluid, which is a semiconductor raw material and contains different elements (illustrative example of the compound semiconductor includes a compound semiconductor of the II-VI groups, a compound semiconductor of the III-V groups, a compound semiconductor of the IV group, a compound semiconductor of the I-III-VI groups).

A reaction to produce semiconductor fine particles by reducing a semiconductor element (illustrative example of the semiconductor element includes an element selected form the group consisting of silicon (Si), germanium (Ge), carbon (C), and tin (Sn)).

A reaction to produce magnetic fine particles by reducing a magnetic raw material (illustrative example of the magnetic raw material includes at least one kind selected from nickel, cobalt, iridium, iron, platinum, gold, silver, manganese, chromium, palladium, yttrium, and lanthanide (neodymium, samarium, gadolinium, and terbium)).

A reaction to separate biologically ingestible fine particles by mixing a fluid which at least one kind of raw material of the biologically ingestible fine particles is dissolved in a first solvent with a solvent capable of becoming a second solvent having lower solubility of the biologically ingestible fine particles than the first solvent.

Alternatively, a reaction to separate biologically ingestible fine particles by a neutralization reaction caused by mixing a fluid containing at least one kind of an acidic substance or a cationic substance with a fluid containing at least one kind of a basic substance or an anionic substance. In the present invention, for example, in the case that barium sulfate fine particles to be ingested into a living body as a contrast agent are separated, a water-soluble barium salt solution as the raw material fluid is mixed with a water-soluble sulfate compound solution including sulfuric acid as the at least one kind of fluid other than the raw material fluid, whereby separating barium sulfate fine particles by a neutralization reaction.

A treatment to obtain microemulsion particles by mixing a fluid to be processed that contains an oil phase component which contains a fat-soluble pharmacologically active substance with a fluid to be processed comprising at least aqueous dispersion solvent, or by mixing a fluid to be processed that contains a aqueous phase component which contains a water-soluble pharmacologically active substance with a fluid to be processed comprising at least an oil-based dispersion solvent.

Alternatively, a treatment to obtain a liposome by mixing a dispersed phase of a fluid to be processed with a continuous phase of a fluid to be processed, wherein at least any one of the dispersed phase or the continuous phase contains one or more kind of phospholipid, the dispersed phase contains a pharmacologically active substance, and the continuous phase is comprised of at least an aqueous dispersion solvent.

A treatment to obtain resin fine particles by mixing a fluid in which a resin is dissolved in a solvent that has solubility and compatibility to the said resin with an aqueous solvent, thereby effecting separation or emulsification; and a treatment to obtain an emulsion by mixing an oil phase component such as a resin and an oil with a water phase component.

Alternatively, a treatment to obtain resin fine particles by mixing a resin in the molten state obtained by heating with a solvent (there is no restriction as to whether it is aqueous or oily), thereby effecting emulsification and dispersion. Further alternatively, a treatment to agglutinate resin fine particles by mixing a dispersion solution of resin fine particles with a compound solution having a compound such as a salt dissolved therein.

Reactions to obtain an organic compound by an organic reaction of an organic compound starting raw material with various reactants, the reactions such as Friedel-Crafts reaction, nitration reaction, addition reaction, elimination reaction, transfer reaction, polymerization reaction, condensation reaction, coupling reaction, acylation, carbonylation, aldehyde synthesis, peptide synthesis, aldol reaction, indole reaction, electrophilic substitution reaction, nucleophilic substitution reaction, Wittig reaction, Michael addition reaction, enamine synthesis, ester synthesis, enzymatic reaction, diazo coupling reaction, oxidation reaction, reducing reaction, multistep reaction, selective addition reaction, Suzuki-Miyaura coupling reaction, Kumada-Corriu reaction, methathesis reaction, isomerization reaction, radical polymerization reaction, anionic polymerization reaction, cationic polymerization reaction, metal-catalyzed polymerization reaction, consecutive reaction, polymer synthesis, acetylene coupling reaction, episulfide synthesis, episulfide synthesis, Bamberger rearrangement, Chapman rearrangement, Claisen condensation, quinoline synthesis, Paal-Knorr furan synthesis, Paal-Knorr pyrole synthesis, Passerini reaction, Paterno-Buchi reaction, carbonyl-ene reaction (Prins reaction), Jacobsen rearrangement, Koenigs-Knorr glucosidation reaction, Leuckart-Wallach reaction, Horner-Wadsworth-Emmons reaction, Gassman reaction, Noyori assymmetric hydrogenation reaction, Perkin reaction, Petasis reaction, Tishchenko reaction, Tishchenko reaction, Ullmann coupling, Nazarov cyclization, Tiffeneau-Demjanov rearrangement, template synthesis, oxidation using selenium dioxide, Reimer-Tiemann reaction, Grob cleavage reaction, haloform reaction, Malaprade glycol oxidative cleavage, Hofmann elimination, thiocarbonylation by using Lawesson reagent, Lossen rearrangement, cyclic ketone synthesis by using FAMSO, Favorskii rearrangement, Feist-Benary furan synthesis, Gabriel amine synthesis, Glaser reaction, Grignard reaction, Cope elimination, Cope rearrangement, diimide reduction of alkynes, Eschenmoser aminomethylation reaction, [2+2] photocyclization reaction, Appel reaction, aza-Wittig reaction, Bartoli indole synthesis, Carroll rearrangement, Chichibabin reaction, Clemmensen reduction, Combes quinoline synthesis, Tsuzi-Trost reaction, TEMPO oxidation, dihydroxylation by using osmium tetraoxide, Fries rearrangement, Neber rearrangement, Barton-McCombie deoxygenation, Barton decarboxylation, Seyferth-Gilbert alkyne synthesis, Pinnick (Kraus) oxidation, Itoh-Saegusa oxidation, Eschenmoser cleavage reaction, Eschenmoser-Claisen rearrangement, Doering-LaFlamme allene synthesis, Corey-Chakovsky reaction, acyloin condensation, Wolff-Kishner reduction, IBX oxidation, Parkin-Doering oxidation, Reissert reaction, Jacobsen's kinetic optical resolution hydrolysis, benzilic acid rearrangement, Hiyama cross-coupling, Luche reduction, oxy merculation, Vilismeier-Haak reaction, Wolff rearrangement, Kolbe-Schmitt reaction, Corey-Kim oxidation, Cannizzaro reaction, Henry reaction, transformation of an alcohol to an alkane, Arndt-Eistert synthesis, hydroformylation reaction, Peterson olefination, decarbonylation reaction, Curtius rearrangement, Wohl-Zeigler bromination at allyl position, Pfitzner-Moffatt oxidation, McMurry coupling, Barton reaction, Balz-Shiemann reaction, Masamune-Bergman reaction, Dieckmann condensation, pinacol coupling, Williamson ether synthesis, iodolactonization reaction, Harries ozone decomposition, oxidation by active manganese dioxide, alkyne cyclotrimerization reaction, Kumada-Tamao-Corriu cross-coupling, syn-β elimination of a sulfoxide and a selnoxide, Fisher indole synthesis, Oppenauer oxidation, Darzens condensation reaction, Alder ene reaction, Sarett-Collins oxidation, Nozaki-Hiyama-Kishi coupling reaction, Weinreb ketone synthesis, DAST fluorination, Corey-Winter olefin synthesis, Hosomi-Sakurai reaction, alcohol oxidation by using PCC (PDC), Jones oxidation, Keck allylation reaction, cyanide addition by using Nagata reagent, Negishi coupling, Ireland-Claisen rearrangement, Baeyer-Villiger oxidation, p-methoxybenzyl (PMB or MPM), dimethoxybenzyl (DMB) protection, deprotection, Wacker oxidation, Myers assymmetric alkylation, Yamaguchi macrolactonization, Mukaiyama-Corey macrolactonization, Bode peptide synthesis, Lindlar reduction, homogeneous hydrogenation, orthometallation, Wagner-Meerwein rearrangement, Wurtz reaction, ketone synthesis by using 1,3-dithiane, Michael addition, ketone synthesis by Stork enamine, Pauson-Khand cyclopentene synthesis, and Tebbe reaction.

EXAMPLES

Hereinafter, the present invention will be explained in more detail by showing Examples; but, the present invention is not limited only to these Examples.

Note that, in the following Examples, the term "from the center" means "from the first introduction part d1" of the fluid processing apparatus shown in FIG. 1, the first fluid refers to the first fluid to be processed, and the second fluid refers to the second fluid to be processed which is introduced from the second introduction member d2 of the fluid processing apparatus shown in FIG. 1. The form of the opening d20 of the fluid processing apparatus shown in FIG. 1 is a concentric circular ring form which surrounds the central opening of the processing surface 2 as shown by the dotted lines in FIG. 2(B).

Examples 1 to 3 and Comparative Examples 1 to 3

Production of Quinacridone Nanoparticles

The separation reaction is done by mixing a quinacridone solution having an organic pigment (C. I. Pigment Red 122, hereinafter PR-122) dissolved in concentrated sulfuric acid with methanol in a thin film fluid formed between the processing surfaces 1 and 2 which are disposed in a position they are faced with each other so as to be able to approach to and separate from each other, at least one of which rotates relative to the other by using the reaction apparatus shown in FIG. 1 which the fluids are uniformly dispersed, stirred, and mixed in the said thin film fluid.

While the PR-122 solution (concentration of 2.0% by weight) having PR-122 powders dissolved in concentrated sulfuric acid was introduced as the first fluid (raw material fluid) from the center with the supply pressure of 0.350 MPa and the back pressure of 0.02 MPa, methanol was introduced as the second fluid into between the processing surfaces (rotation number of 1500 rpm).

The first fluid and the second fluid were mixed in the thin film fluid, and the dispersion solution of the PR-122 fine particles was discharged from the processing surfaces 1 and 2. The PR-122 fine particles in the discharged dispersion solution of the PR-122 fine particles were loosely aggregated, collected by filtration using a filter cloth with opening of 1.0 μm, and then washed by pure water to obtain a wet cake of the PR-122 fine particles. A part of the wet cake of the PR-122 fine particles was diluted by an aqueous surfactant solution of NEOGEN R-K (manufactured by Dai-ichi Kogyo Seiyaku Co., Ltd.), and then redispersed by using a rotating disperser Clearmix CLM-2.2S (trade name; manufactured by M. Technique Co., Ltd.) to obtain a dispersion solution of PR-122.

The obtained dispersion solution of the PR-122 was diluted, put on a collodion film, and then, the particle diameter of the primary particle thereof was confirmed by the TEM observation. The TEM observation was conducted by using JEM-2100 (manufactured by JEOL Ltd.) to measure the particle diameter of the primary particle in a plurality of observation spots with the observation magnification of 20,000; and the average value thereof was used.

The first fluid, the second fluid, the production volume of the PR-122 fine particles, and the particle diameter of the primary particle thereof (shown by "particle diameter" in Table 1) are shown in Table 1.

From Table 1, it can be seen that the production volume is readily increased by using the PR-122 solution containing the PR-122 which is the fine particle raw material as the first fluid (raw material fluid).

Examples 4 to 6 and Comparative Examples 4 to 6

Production of Silver Nanoparticles

The reduction reaction was done by mixing an aqueous silver nitrate solution having silver nitrate dissolved in pure water, sodium borohydride as a reducing agent, and Thiokalcol 08 (manufactured by Kao Corporation) as a surfactant with a reducing agent solution dissolved in a mixed solvent of methanol and toluene in a thin film fluid formed between the processing surfaces 1 and 2 which are disposed in a position they are faced with each other so as to be able to approach to and separate from each other, at least one of which rotates relative to the other, in the reaction apparatus shown FIG. 1 which uniformly disperses, stirs, and mixes in the thin film fluid.

While the silver nitrate solution (concentration of 5.0% by weight) having silver nitrate dissolved in pure water was introduced as the first fluid (raw material fluid) from the center with the supply pressure of 0.300 MPa and the back pressure of 0.02 MPa, the reducing agent solution was introduced as the second fluid into between the processing surfaces (rotation number of 2000 rpm).

The first fluid and the second fluid were mixed in the thin film fluid, and the dispersion solution of silver nanoparticles was discharged from the processing surfaces 1 and 2. The silver nanoparticles in the discharged dispersion solution of the silver nanoparticles were loosely aggregated, collected by filtration using a filter cloth with opening of 1.0 μm, and then washed by methanol and toluene to obtain a wet cake of silver nanoparticles. Apart of the wet cake of silver nanoparticles was diluted by toluene, and then dispersed by

TABLE 1

| | First fluid | | Second fluid | | Particle diameter (nm) | Production volume (g/minute) |
|---|---|---|---|---|---|---|
| | Kind | Introduction rate (mL/minute) | Kind | Introduction rate (mL/minute) | | |
| Example | | | | | | |
| 1 | PR-122 in $H_2SO_4$ | 50 | Methanol | 70 | 10 | 1.8 |
| 2 | (2.0% by weight) | 200 | | 85 | 10 | 7.4 |
| 3 | | 600 | | 100 | 20 | 22.1 |
| Comparative Example | | | | | | |
| 1 | Methanol | 400 | PR-122 in $H_2SO_4$ | 5 | 10 | 0.2 |
| 2 | | 600 | (2.0% by weight) | 10 | 20 | 0.4 |
| 3 | | 1000 | | 50 | 50 | 1.8 |

Note that, in the apparatus used in these Examples and Comparative Examples, the opening d20 of the another introduction part d2 as shown above which was formed of one concentric circular ring form surrounding the central opening of the processing surface 2 was used, and the ratio (a/b) of the total open area (a) of the space between both processing surfaces to the total open area (b) of the opening leading to the different introduction part was set at 1.0 in Example 1, 2.0 in Example 2, 5.0 in Example 3, 5.6 in Comparative Example 1, 25.0 in Comparative Example 2, and 100.0 in Comparative Example 3.

using an ultrasonic cleaning machine to obtain a dispersion solution of silver nanoparticles.

The obtained dispersion solution of the silver nanoparticles was diluted, put on a collodion film, and then, the particle diameter of the primary particle thereof was confirmed by the TEM observation. The TEM observation was conducted by using JEM-2100 (manufactured by JEOL Ltd.) to measure the particle diameter of the primary particle in a plurality of observation spots with the observation magnification of 20,000; and the average value thereof was used.

The first fluid, the second fluid, the production volume of the silver nanoparticles, and the particle diameter of the primary particle thereof (shown by "particle diameter" in Table 2) are shown in Table 2.

ing PVP dissolved in pure water in a thin film fluid formed between the processing surfaces 1 and 2 which are disposed in a position they are faced with each other so as to be able to approach to and separate from each other, at least one of

TABLE 2

| | First fluid | | Second fluid | | | |
|---|---|---|---|---|---|---|
| | Kind | Introduction rate (mL/minute) | Kind | Introduction rate (mL/minute) | Particle diameter (nm) | Production volume (g/minute) |
| Example | | | | | | |
| 4 | Aqueous silver nitrate solution | 100 | NaBH$_4$ (5.0% by weight) | 60 | 5 | 3.2 |
| 5 | (5.0% by weight) | 200 | Thiokalcol 08 (0.015% by weight) | 60 | 5 | 6.4 |
| 6 | | 400 | Methanl:toluene = 1:1 mixed solvent (94.985% by weight) | 100 | 7 | 12.7 |
| Comparative Example | | | | | | |
| 4 | NaBH$_4$ (0.05% by weight) | 300 | Aqueous silver nitrate solution | 5 | 5 | 0.2 |
| 5 | Thiokalcol 08 (0.015% by weight) | 600 | (5.0% by weight) | 10 | 7 | 0.3 |
| 6 | Methanl:toluene = 1:1 mixed solvent (99.935% by weight) | 1000 | | 40 | 15 | 1.3 |

Note that, in the apparatus used in these Examples and Comparative Examples, the opening d20 of the another introduction part d2 as shown above which was formed of one concentric circular ring form surrounding the central opening of the processing surface 2 was used, and the ratio (a/b) of the total open area (a) of the space between both processing surfaces to the total open area (b) of the opening leading to the different introduction part was set at 0.5 in Example 4, 0.8 in Example 5, 3.8 in Example 6, 8.0 in Comparative Example 4, 40.0 in Comparative Example 5, and 80.0 in Comparative Example 6.

From Table 2, it can be seen that the production volume is readily increased by using the silver nitrate solution containing the silver nitrate which is the fine particle raw material as the first fluid (raw material fluid).

Examples 7 to 9 and Comparative Examples 7 to 9

Production of Resin Emulsion

Emulsification is done by mixing an acryl resin monomer with an aqueous polyvinyl pyrrolidone (PVP) solution hav- which rotates relative to the other, in the reaction apparatus shown in FIG. 1 which uniformly disperses, stirs, and mixes in the thin film fluid.

While the acryl resin monomer was introduced as the first fluid (raw material fluid) from the center with the supply pressure of 0.15 MPa and the back pressure of 0.00 MPa, the aqueous PVP solution was introduced as the second fluid into between the processing surfaces.

The first fluid and the second fluid were mixed and emulsified in the thin film fluid, and a solution containing the acryl resin monomer emulsion was discharged from the processing surfaces 1 and 2.

Particle diameter of the obtained acryl resin monomer emulsion was measured by using the particle diameter distribution measurement apparatus SALD-7000 (manufactured by Shimadzu Corporation).

The first fluid, the second fluid, the production volume of the acryl resin monomer emulsion, and the volume-average particle diameter (shown by "particle diameter" in Table 3) obtained from the particle diameter distribution measurement results are shown in Table 3.

TABLE 3

| | | First fluid | | Second fluid | | | |
|---|---|---|---|---|---|---|---|
| Example | Rotation number (rpm) | Kind | Introduction rate (mL/minute) | Kind | Introduction rate (mL/minute) | Particle diameter (μm) | Production volume (mL/minute) |
| 7 | 3000 | Acryl resin monomer | 30 | Aqueous PVP solution (3.0% by weight) | 100 | 1.38 | 30 |
| 8 | 2500 | | 50 | | 100 | 5.74 | 50 |
| 9 | 2500 | | 100 | | 100 | 11.36 | 100 |

| | | First fluid | | Second fluid | | | |
|---|---|---|---|---|---|---|---|
| Comparative Example | Rotation number (rpm) | Kind | Introduction rate (mL/minute) | Kind | Introduction rate (mL/minute) | Particle diameter (nm) | Production volume (mL/minute) |
| 7 | 5000 | Aqueous PVP solution (3.0% by weight) | 30 | Acryl resin monomer | 0.5 | 1.34 | 0.5 |
| 8 | 4000 | | 50 | | 1.0 | 5.86 | 1.0 |
| 9 | 4000 | | 100 | | 5.0 | 10.98 | 5.0 |

Note that, in the apparatus used in these Examples and Comparative Examples, the opening d20 of the another introduction part d2 as shown above which was formed of one concentric circular ring form surrounding the central opening of the processing surface 2 was used, and the ratio (a/b) of the total open area (a) of the space between both processing surfaces to the total open area (b) of the opening leading to the different introduction part was set at 1.5 in Example 7, 3.5 in Example 8, 4.5 in Example 9, 8.5 in Comparative Example 7, 10.0 in Comparative Example 8, and 60.0 in Comparative Example 9.

From Table 3, it can be seen that the production volume is readily increased by using the acryl resin monomer emulsion which is the fine particle raw material as the first fluid (raw material fluid).

Examples 10 to 12 and Comparative Examples 10 to 12

Production of Titanium Oxide

Separation of titanium oxide is done by mixing a titanium compound solution having titanium tetraisopropoxide (TiOiPr) and acetylacetone dissolved in isopropyl alcohol (IPA) with an aqueous ammonia solution in a thin film fluid formed between the processing surfaces 1 and 2 which are disposed in a position they are faced with each other so as to be able to approach to and separate from each other, at least one of which rotates relative to the other, in the reaction apparatus shown in FIG. 1 which uniformly disperses, stirs, and mixes in the thin film fluid.

While the titanium compound solution was introduced as the first fluid (raw material fluid) from the center with the supply pressure of 0.30 MPa and the back pressure of 0.02 MPa, the aqueous ammonia solution was introduced as the second fluid into between the processing surfaces (rotation number of 1700 rpm).

The first fluid and the second fluid were mixed in the thin film fluid, and the dispersion solution of the titanium oxide nanoparticles was discharged from the processing surfaces 1 and 2, and then, the discharged dispersion solution of the titanium oxide nanoparticles was mixed with the same amount of an aqueous nitric acid solution (4.5% by weight). The titanium oxide nanoparticles in the obtained dispersion solution of the titanium oxide nanoparticles were loosely aggregated, and then the titanium oxide nanoparticles were spun down by using a centrifugal separator. After removing the impurity, the titanium oxide nanoparticles were washed by pure water to obtain a wet cake of the titanium oxide nanoparticles. A part of the wet cake of the titanium oxide nanoparticles was diluted with pure water and then dispersed by using an ultrasonic cleaning machine to obtain a dispersion solution of the titanium oxide nanoparticles.

The obtained dispersion solution of the titanium oxide nanoparticles was diluted, put on a collodion film, and then, the particle diameter of the primary particle thereof was confirmed by the TEM observation. The TEM observation was conducted by using JEM-2100 (manufactured by JEOL Ltd.) to measure the particle diameter of the primary particle in a plurality of observation spots with the observation magnification of 20,000; and the average value thereof was used.

Figure 5:
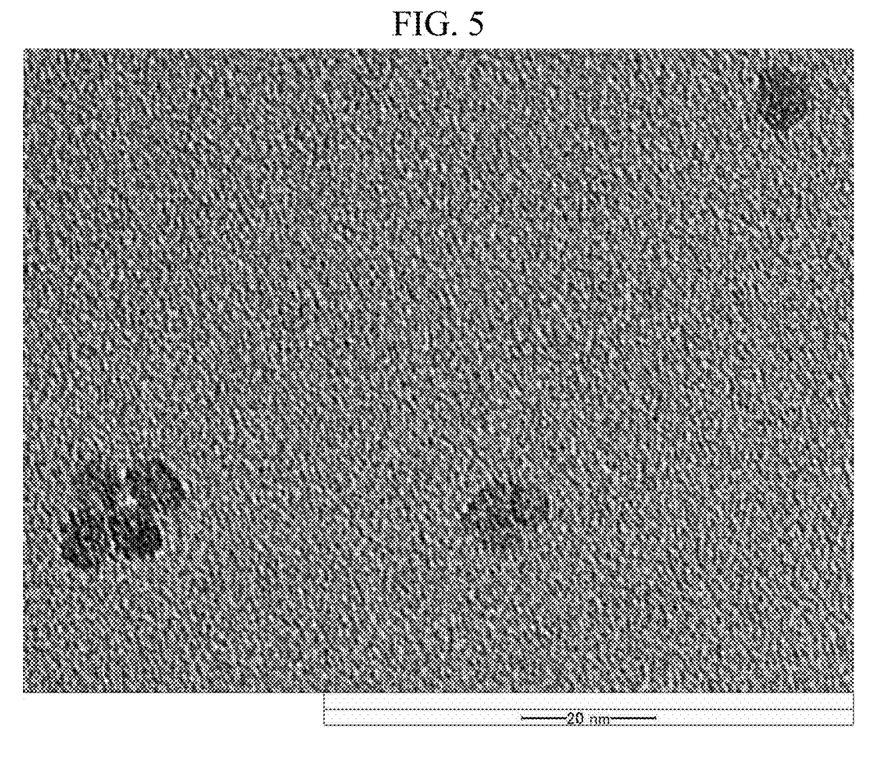
FIG. 5 is the TEM picture of the titanium oxide nanoparticles obtained in Example 11.

The first fluid, the second fluid, the production volume of the titanium oxide nanoparticles, and the particle diameter of the primary particle thereof (shown by "particle diameter" in Table 4) are shown in Table 4. The TEM picture of the titanium oxide nanoparticles produced in Example 11 is shown in FIG. 5.

TABLE 4

| | First fluid | | Second fluid | | | |
|---|---|---|---|---|---|---|
| | Kind | Introduction rate (mL/minute) | Kind | Introduction rate (mL/minute) | Particle diameter (nm) | Production volume (g/minute) |
| Example | | | | | | |
| 10 | IPA solution of titanium tetraisopropoxide (TiOiPr, 5% by weight)-acetylacetone (1% by weight) | 100 | Aqueous ammonia solution (10% by weight) | 10 | 5 | 1.1 |
| 11 | | 200 | | 20 | 10 | 2.2 |
| 12 | | 400 | | 40 | 10 | 4.4 |
| Comparative Example | | | | | | |
| 10 | Aqueous ammonia solution (1% by weight) | 100 | IPA solution of titanium tetraisopropoxide (TiOiPr, 5% by weight)-acetylacetone (1% by weight) | 10 | 5 | 0.1 |
| 11 | | 200 | | 20 | 10 | 0.2 |
| 12 | | 400 | | 40 | 10 | 0.4 |

Note that, in the apparatus used in these Examples and Comparative Examples, the opening d20 of the another introduction part d2 as shown above which was formed of one concentric circular ring form surrounding the central opening of the processing surface 2 was used, and the ratio (a/b) of the total open area (a) of the space between both processing surfaces to the total open area (b) of the opening leading to the different introduction part was set at 0.4 in Example 10, 0.8 in Example 11, 2.8 in Example 12, 8.0 in Comparative Example 10, 35.0 in Comparative Example 11, and 75.0 in Comparative Example 12.

From Table 4, it can be seen that the production volume is readily increased by using the titanium compound solution containing the titanium tetraisopropoxide which is the fine particle raw material as the first fluid (raw material fluid).

1 first processing surface
2 second processing surface
10 first processing member
11 first holder
20 second processing member
21 second holder
d1 first introduction part d2 second introduction part
d20 opening
p fluid pressure imparting mechanism

The invention claimed is:

1. A method comprising the steps of:
preparing at least two fluids, including a first fluid and a second fluid, the first fluid being a raw material fluid which contains at least one kind of the fine particle raw material, the second fluid being a fluid to process the fine particle raw material;
introducing the at least two fluids into a processing device, the processing device comprising at least two processing surfaces facing each other, the at least two processing surfaces being operable to approach to and separate from each other, wherein at least one of the at least two processing surfaces is in the form of a ring and rotates relative to the other;
mixing the at least two fluids in a space formed between the at least two processing surfaces, thereby forming a thin film fluid between the at least two processing surfaces; and
obtaining fine particles from the thin film fluid,
wherein the raw material fluid is introduced from a center of the at least two processing surfaces into the space between the at least two processing surfaces via a first introduction path, the processing device includes a second introduction path independent of the first introduction path, the second introduction path forming at least one opening, which is formed on at least one of the at least two processing surfaces and leading to the space between the at least two processing surfaces, and wherein the second fluid is introduced into the space between the at least two processing surfaces via the second introduction path and the at least one opening, and
wherein a ratio of a total open area (a) to a total open area (b) is no more than 5, wherein:
the total open area (a) is obtained by multiplying a circumference of a circle having a radius which is a distance from a center of the ring to a point from which the first fluid and the second fluid start joining together, by a distance between the at least two processing surfaces in a direction along a rotation axis of the at least one processing surface; and
the total open area (b) is a sum of introduction opening areas of the at least one opening formed on the at least one processing surface.

2. The method according to claim 1, wherein the fine particles are obtained by at least one process selected from separation, emulsification, dispersion, reaction, and aggregation.

3. The method according to claim 1, wherein the processing device includes at least two or more openings leading to the space between the at least two processing surfaces, and a total open area (a) is no more than 5 times, relative to each open area of the openings that lead to the second introduction path.

4. The method according to claim 3, wherein a form of the at least one opening of the second introduction flow path leading to the space between the at least two processing surfaces is a circular ring.

5. The method according to claim 3, wherein a flow amount based on volume per unit time of the raw material fluid introduced into the space between the at least two processing surfaces from the center of this ring is in the range of 0.1 to 20000 times relative to a flow amount based on volume per unit time of the second fluid that is introduced from the at least one opening.

6. The method according to claim 1, wherein a form of the at least one opening of the second introduction flow path leading to the space between the at least two processing surfaces is a circular ring.

7. The method according to claim 6, wherein a flow amount based on volume per unit time of the raw material fluid introduced into the space between the at least two processing surfaces from the center of this ring is in the range of 0.1 to 20000 times relative to a flow amount based on volume per unit time of the second fluid that is introduced from the at least one opening.

8. The method according to claim 1, wherein a flow amount based on volume per unit time of the raw material fluid introduced into the space between the at least two processing surfaces from the center of this ring is in the range of 0.1 to 20000 times relative to a flow amount based on volume per unit time of the second fluid that is introduced from the at least one opening.

* * * * *